US010441204B1

United States Patent
Edlin et al.

(10) Patent No.: US 10,441,204 B1
(45) Date of Patent: Oct. 15, 2019

(54) METHODS FOR OBTAINING BLOOD FROM A SUBJECT

(71) Applicant: Theranos IP Company, LLC, Healdsburg, CA (US)

(72) Inventors: Daniel Edlin, Palo Alto, CA (US); Nicholas Menchel, Palo Alto, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 14/220,013

(22) Filed: Mar. 19, 2014

Related U.S. Application Data (60) Provisional application No. 61/803,449, filed on Mar. 19, 2013, provisional application No. 61/874,893, filed on Sep. 6, 2013.

(51) Int. Cl.
*A61B 5/15* (2006.01)
*G09B 23/28* (2006.01)
*A61B 5/157* (2006.01)

(52) U.S. Cl.
CPC ........ *A61B 5/150068* (2013.01); *G09B 23/28* (2013.01); *A61B 5/157* (2013.01); *A61B 5/150022* (2013.01); *A61B 5/150412* (2013.01)

(58) Field of Classification Search
CPC .............. A61B 5/157; A61B 5/150412; A61B 5/150022; A61B 5/150068
USPC .................................................. 600/573–583
See application file for complete search history.

(56) References Cited

U.S. PATENT DOCUMENTS

| | | | | |
|---|---|---|---|---|
| 5,518,006 | A * | 5/1996 | Mawhirt | A61B 5/15142 600/583 |
| 2006/0210429 | A1* | 9/2006 | Hunsley | B01L 3/5082 422/550 |
| 2007/0089677 | A1* | 4/2007 | Sagiv | A01J 5/02 119/14.02 |
| 2009/0177224 | A1* | 7/2009 | Naghavi | A61B 5/150022 606/203 |
| 2009/0312781 | A1* | 12/2009 | Hyoue | A61B 5/1411 606/181 |
| 2011/0124984 | A1* | 5/2011 | Rostaing | B01L 3/5023 600/309 |
| 2011/0125058 | A1* | 5/2011 | Levinson | A61B 5/14514 600/578 |
| 2014/0073990 | A1* | 3/2014 | Holmes | B01L 3/502 600/575 |

OTHER PUBLICATIONS

Wiodietcorp "How to: Blood Test Using LDX" youtube video published on Aug. 29, 2012, https://youtu.be/4jCcrAnwlw0.*
"Capillary Puncture" by keymcp published May 13, 2009 https://youtu.be/Wg-U7GISGAk.*
USFoodandDrugAdmin, Preventing Bloodborne Infections When Using Fingerstick Devices https://youtu.be/W77W8SN6KOQ Nov. 18, 2010, Time 2:03-2:12.*
Blood Glucose Monitoring by knust oer, https://youtu.be/eBUUyO_hEDM, Nov. 28, 2011.*

(Continued)

*Primary Examiner* — Sean P Dougherty (57) ABSTRACT

Provided herein are methods for extracting blood from a subject's digit, such as a finger. Methods provided herein may release relatively large quantities of blood from a pierced finger. Pressure can be applied at selected locations on the subject's digit to increase blood flow released from the subject.

18 Claims, 8 Drawing Sheets

(56) References Cited

OTHER PUBLICATIONS

Chapter 10 Capillary Puncture Equipment and Procedures 2012 Wolters Kluwer.*
"Recommended Procedure for the Collection of Blood Lead Specimens by Fingerstick", Wisconsin State Laboratory of Hygiene, Apr. 2008.*
How to Obtain a Blood Sample using an Accu-Check Safe-T-Pro (https://youtu.be/8AuMGu6ExwY) published on Jun. 29, 2012.*

\* cited by examiner

METHODS FOR OBTAINING BLOOD FROM A SUBJECT

CROSS-REFERENCE TO RELATED APPLICATIONS

This application claims the benefit of, and priority to U.S. Provisional Patent Application No. 61/803,449, filed Mar. 19, 2013, and U.S. Provisional Patent Application No. 61/874,893, filed Sep. 6, 2013, the contents of which are hereby incorporated by reference in their entirety for all purposes.

BACKGROUND

For medical testing and other purposes, it is frequently desirable to obtain a sample of blood from a subject. A variety of methods for releasing blood from a subject are known in the art. One common method for releasing blood is a fingerstick. Fingersticks are generally simple to perform and relatively painless. However, typically, only a small volume of blood is obtained from a fingerstick, thus limiting the number and type of tests that may be performed with blood obtained from a fingerstick. Another common method for releasing blood is a venous draw with a needle. While needle-based venous draws can release a large volume of blood from a subject, needle-based venous draws require a skilled technician to perform, are relatively painful, and frequently cause may cause anxiety in a subject.

Accordingly, improvements in methods for obtaining blood from a subject are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

SUMMARY

At least some of disadvantages associated with the prior art are overcome by at least some or all of the embodiments described in this disclosure. Although the embodiments herein are typically described in the context of obtaining a blood sample, it should be understood that the embodiments herein are not limited to blood samples and can also be adapted to acquire other fluid(s) or bodily sample(s) for analysis.

In some embodiments, provided herein is a method of releasing blood from a subject's digit, the method comprising: applying pressure to 1) a proximal phalanx of the digit and 2) one or both of an intermediate phalanx and a distal phalanx of the digit, while pressure is maintained on the proximal phalanx and said one or both of the intermediate phalanx and the distal phalanx, piercing a site on the distal phalanx, wherein blood is released from the site pierced on the distal phalanx. In some embodiments, the method may further comprise: releasing pressure from the proximal phalanx and said one or both of the intermediate phalanx and distal phalanx, reapplying and maintaining pressure to the proximal phalanx, and while pressure is maintained on the proximal phalanx, reapplying and maintaining pressure to one or both of the intermediate phalanx and the distal phalanx, wherein blood is released from the site pierced on the distal phalanx.

In some embodiments, provided herein is a method of releasing blood from a subject's digit, the method comprising: A method of releasing blood from a subject's digit, comprising: piercing a site on a distal phalanx of the digit, and applying pressure to 1) a proximal phalanx of the digit and 2) one or both of an intermediate phalanx and the distal phalanx of the digit, wherein blood is released from the site pierced on the distal phalanx. In some embodiments, the method may further comprise: releasing pressure from the proximal phalanx and said one or both of the intermediate phalanx and distal phalanx, reapplying and maintaining pressure to the proximal phalanx, and while pressure is maintained on the proximal phalanx, reapplying and maintaining pressure to one or both of the intermediate phalanx and the distal phalanx, wherein blood is released from the site pierced on the distal phalanx.

In some embodiments, provided herein is a method of releasing blood from a subject's digit, the method comprising: first, applying and maintaining pressure to a proximal phalanx of the digit, second, while pressure is maintained on the proximal phalanx, applying and maintaining pressure to one or both of an intermediate phalanx and a distal phalanx of the digit, third, while pressure is maintained on the proximal phalanx and said one or both of the intermediate phalanx and distal phalanx, piercing a site on the distal phalanx, wherein blood is released from the site pierced on the distal phalanx, fourth, while pressure is maintained on the proximal phalanx, releasing pressure on said one or both of the intermediate phalanx and distal phalanx, fifth, while pressure is maintained on the proximal phalanx, reapplying and maintaining pressure to one or both of the intermediate phalanx and the distal phalanx, wherein blood is released from the site pierced on the distal phalanx. In some embodiments, the method may further comprise: sixth, releasing pressure from the proximal phalanx and said one or both of the intermediate phalanx and distal phalanx, seventh, reapplying and maintaining pressure to the proximal phalanx, and eighth, while pressure is maintained on the proximal phalanx, reapplying and maintaining pressure to one or both of the intermediate phalanx and the distal phalanx, wherein blood is released from the site pierced on the distal phalanx.

In some embodiments, provided herein is a method of releasing blood from a subject's digit, the method comprising: first, piercing a site on a distal phalanx of the digit, second, applying and maintaining pressure to a proximal phalanx of the digit, third, while pressure is maintained on the proximal phalanx, applying and maintaining pressure to one or both of an intermediate phalanx and a distal phalanx of the digit, wherein blood is released from the site pierced on the distal phalanx. In some embodiments, the method may further comprise: fourth, releasing pressure from the proximal phalanx and said one or both of the intermediate phalanx and distal phalanx, fifth, reapplying and maintaining pressure to the proximal phalanx, and sixth, while pressure is maintained on the proximal phalanx, reapplying and maintaining pressure to one or both of the intermediate phalanx and the distal phalanx, wherein blood is released from the site pierced on the distal phalanx.

In some embodiments, provided herein is a method of releasing blood from a subject's digit, the method comprising: first, piercing a site on a distal phalanx of the digit, second, applying and maintaining pressure to a proximal phalanx of the digit, third, while pressure is maintained on the proximal phalanx, applying and maintaining pressure to one or both of an intermediate phalanx and a distal phalanx of the digit, wherein blood is released from the site pierced on the distal phalanx, fourth, while pressure is maintained on the proximal phalanx, releasing pressure on said one or both of the intermediate phalanx and distal phalanx, and fifth, while pressure is maintained on the proximal phalanx, reapplying and maintaining pressure to one or both of the intermediate phalanx and the distal phalanx, wherein blood is released from the site pierced on the distal phalanx. In some embodiments, the method may further comprise: sixth, releasing pressure from the proximal phalanx and said one or both of the intermediate phalanx and distal phalanx, seventh, reapplying and maintaining pressure to the proximal phalanx, and eighth, while pressure is maintained on the proximal phalanx, reapplying and maintaining pressure to one or both of the intermediate phalanx and the distal phalanx, wherein blood is released from the site pierced on the distal phalanx.

In some embodiments, in methods provided herein involving applying or maintaining pressure to a proximal phalanx, intermediate phalanx, distal phalanx, or digit, pressure is applied or maintained to the digit or phalanx without using a sliding or translational motion to apply pressure against the digit or phalanx.

In some embodiments, in methods provided herein involving applying pressure to 1) a proximal phalanx of the digit and 2) one or both of an intermediate phalanx and a distal phalanx of the digit, pressure is applied to the subject's digit in a sequential manner, wherein pressure is first applied to the proximal phalanx and then pressure is applied to said one or both of the intermediate phalanx and the distal phalanx.

In some embodiments, in a method provided herein involving 1) applying and maintaining of pressure to the proximal phalanx and 2) the applying and maintaining of pressure to said one or both of the intermediate phalanx and distal phalanx, at least one of 1) the applying and maintaining of pressure to the proximal phalanx or 2) the applying and maintaining of pressure to said one or both of the intermediate phalanx and distal phalanx, is performed by one or more fingers of a hand of a human technician, wherein the fingers are selected from a thumb, an index finger, a middle finger, an ring finger, and a small finger.

In some embodiments, in a method provided herein involving 1) applying and maintaining of pressure to the proximal phalanx and 2) the applying and maintaining of pressure to said one or both of the intermediate phalanx and distal phalanx, both of 1) the applying and maintaining of pressure to the proximal phalanx or 2) the applying and maintaining of pressure to said one or both of the intermediate phalanx and distal phalanx, is performed by one or more fingers of a hand of a human technician, wherein the fingers are selected from a thumb, an index finger, a middle finger, an ring finger, and a small finger.

In some embodiments, in methods provided herein involving applying and maintaining pressure to the proximal phalanx, the applying and maintaining pressure to the proximal phalanx is performed by fingers comprising the thumb and index finger.

In some embodiments, in methods provided herein involving applying and maintaining pressure to one or both intermediate phalanx and distal phalanx, the applying and maintaining pressure to said one or both intermediate phalanx and distal phalanx is performed by one or more fingers comprising the middle finger.

In some embodiments, methods provided herein comprise warming the digit prior to any other steps of the method. In some embodiments, warming the digit comprises contacting the digit with a material having a temperature of at least 25, 30, 35, 40, 45, or 50° C.

In some embodiments, during a method provided herein, at total of at least 50, 75, 100, 125, 150, 175, or 200 microliters of blood is released from the subject's digit.

In some embodiments, during a method provided herein, the distal phalanx is maintained at a lower elevation than the elevation of the proximal phalanx.

In some embodiments, during a method provided herein, the digit is pierced with a needle having an outer diameter of no greater than 2, 1.8, 1.6, 1.5, 1.4, 1.3, 1.2, 1.1, 1.0, 0.9, 0.8, 0.7, 0.6, 0.5, 0.4, or 0.3 mm. In some embodiments, during a method provided herein, the digit is pierced with a needle having a gauge of 15, 16, 17, 18, 19, 20, 21, 22, 23, 24, 25, 26, 27, 28, 29, 30, 31, 32, or higher (i.e. a greater number, such as 40). In some embodiments, during a method provided herein, the digit is pierced with a blade or lancet having a greatest width of no greater than 2, 1.8, 1.6, 1.5, 1.4, 1.3, 1.2, 1.1, 1.0, 0.9, 0.8, 0.7, 0.6, 0.5, 0.4, or 0.3 mm. In some embodiments, during a method provided herein, the digit is pierced with a needle, blade, or lancet having a length (for penetrating the digit) of no greater than 4, 3.5, 3, 2.5, 2.4, 2.3, 2.2, 2.1, 2, 1.9, 1.8, 1.7, 1.6, 1.5, 1.4, 1.3, 1.2, 1.1, 1.0, 0.9, 0.8, 0.7, 0.6, 0.5, 0.4, or 0.3 mm.

In some embodiments, in a method provided herein involving applying and maintaining of pressure to the proximal phalanx, the applying and maintaining of pressure to the proximal phalanx comprises applying pressure along all points of a perimeter of the proximal phalanx.

In some embodiments, in a method provided herein involving applying and maintaining of pressure to the proximal phalanx, the applying and maintaining of pressure to the proximal phalanx comprises applying pressure along at least a palm-side perimeter half of the proximal phalanx.

In some embodiments, in a method provided herein involving applying and maintaining of pressure to the proximal phalanx, the applying and maintaining of pressure to the proximal phalanx comprises applying pressure along at least a fingernail-side perimeter half of the proximal phalanx.

In some embodiments, in a method provided herein involving applying and maintaining of pressure to the proximal phalanx, the applying and maintaining of pressure to the proximal phalanx comprises applying pressure along at least 50% of a perimeter of the proximal phalanx.

In some embodiments, in a method provided herein, the digit is a thumb, an index finger, a middle finger, a ring finger, or a small finger.

In some embodiments, a method provided herein may further comprise contacting released blood from a digit with a channel of a blood collection device. In some embodiments, the channel of the blood collection device has a perimeter of no greater than 25, 24, 23, 22, 21, 20, 19, 18, 17, 16, 15, 14, 13, 12, 11, 10, 9, 8, 7, 6, 5, 4, 3, 2, or 1 millimeter.

In some embodiments, in a method provided herein comprising applying and maintaining of pressure to a proximal phalanx, two fingers are used for applying and maintaining of pressure to the proximal phalanx.

In some embodiments, in a method provided herein comprising applying and maintaining of pressure to a proximal phalanx, a tourniquet is used for applying and maintaining of pressure to the proximal phalanx.

In some embodiments, in a method provided herein comprising applying and maintaining of pressure to a distal phalanx pressure is applied to both the palm-side and fingernail-side of the distal phalanx.

In embodiments, in a method provided herein involving maintaining pressure to one or more phalanges, pressure is maintained on the one or more phalange for at least 1, 2, 3, 4, 5, 6, 7, 8, 9, 10, 15, 20, 30, 40, 50, 60, 90, or 120 seconds. In embodiments, in a method provided herein involving maintaining pressure to one or more phalanges, pressure is maintained on the one or more phalange for no more than 1, 2, 3, 4, 5, 6, 7, 8, 9, 10, 15, 20, 30, 40, 50, 60, 90, or 120 seconds. In embodiments, in a method provided herein involving maintaining pressure to one or more phalanges, pressure is maintained on the one or more phalange for at least 1, 2, 3, 4, 5, 6, 7, 8, 9, 10, 15, 20, 30, 40, 50, 60, or 90 seconds and no more than 2, 3, 4, 5, 6, 7, 8, 9, 10, 15, 20, 30, 40, 50, 60, 90, or 120 seconds.

In embodiments, in methods provided herein involving releasing pressure from one or more of a proximal phalanx, intermediate phalanx, and distal phalanx (e.g. a proximal phalanx and one or both of an intermediate phalanx and distal phalanx), pressure may be reapplied to one or more of the proximal phalanx, intermediate phalanx, and distal phalanx. In embodiments, pressure may be applied to the phalanx(s) one or more of the proximal phalanx, intermediate phalanx, and distal phalanx at the same time, or in a sequential order. For example, in embodiments, pressure may be reapplied to the proximal phalanx, and then to one or both of the intermediate phalanx and distal phalanx. In other embodiments, pressure may be reapplied to each of the proximal phalanx, intermediate phalanx, and distal phalanx at the same time.

In embodiments of methods provided herein, blood may be collected from a pierced digit after pressure is maintained on one or more phalanx of the digit for a set amount of time. In embodiments, the set amount of time may be at least 1, 2, 3, 4, 5, 6, 7, 8, 10, 15, 20, or 30 seconds. In embodiments, the set amount of time may be no more than 2, 3, 4, 5, 6, 7, 8, 10, 15, 20, 30, or 60 seconds. In embodiments, the set amount of time may be at least 1, 2, 3, 4, 5, 6, 7, 8, 10, 15, 20, or 30 seconds, and no more than 2, 3, 4, 5, 6, 7, 8, 10, 15, 20, 30, or 60 seconds. In embodiments of methods provided herein, blood may be collected from a pierced digit after pressure is maintained on one or both of an intermediate phalanx and distal phalanx for a set amount of time.

In embodiments, blood obtained from a pierced digit according to a method provided herein may be collected into a blood collection device at one, two, three, four, five, more instances. For example, pressure may be applied to a subject's digit according to a method provided herein, and blood may accumulate at the piercing site on the subject's digit. The accumulated blood at the piercing site may be collected, and then pressure may be reapplied to a subject's digit again according to a method provided herein. More blood may accumulate at the piercing site during the performance of a method provided herein, which may be collected. This process may be repeated any number of times.

In embodiments, provided herein is a method of teaching a technician to obtain blood from a subject's digit, wherein the method comprises providing the technician with instructions for releasing blood from a subject's digit according any method provided herein.

In embodiments provided herein involving providing a technician with instructions for releasing blood from a subject's digit according any method provided herein, the instructions may be provided in written form. Written form includes writings on permanent or semi-permanent display formats (e.g. on paper), and also temporary display formats (e.g. electronic writing displayed on the screen of a computerized device). Thus, for example, written instructions may be provided on a loose sheet of paper, in a folded pamphlet, in a paper book or magazine, on a web-page, in an electronic book or magazine, or stored in a portable data storage device (e.g. a compact disc (CD), digital video disc (DVD), USB drive, or flash memory card).

In embodiments provided herein involving providing a technician with instructions for releasing blood from a subject's digit according any method provided herein, the instructions may be provided via live person-to-person instructions. During live person-to-person instructions, a live instructor in the near vicinity of one or more technicians to be trained provides the technician to be trained with instructions for performing a method provided herein. For example, the instructor may be in the same room as, or may be sitting next to a technician to be trained. In embodiments, an instructor provides live person-to-person instructions in a room containing multiple technicians to be trained. In embodiments, an instructor may provide live person-to-person instructions by performing a method as described herein (or a simulation thereof) on the technician to be trained.

In embodiments provided herein involving providing a technician with instructions for releasing blood from a subject's digit according any method provided herein, the instructions may be provided by recorded audio or video instructions. The recorded audio or video instructions may be provided, for example, on a portable data storage device (e.g. a compact disc (CD), digital video disc (DVD), USB drive, or flash memory card), or from a server (e.g. available on-demand over the internet).

In embodiments provided herein involving providing a technician with instructions for releasing blood from a subject's digit according any method provided herein, the technician may also be provided with a model hand or digit with which to practice a method provided herein. The model hand or digit may be made of any suitable material (e.g. plastic, rubber, etc.).

In embodiments, provided herein is a kit for releasing blood from a subject, the kit comprising instructions for releasing blood from a subject's digit according to any method provided herein. In embodiments, instructions in a kit for releasing blood from a subject's digit according to any method provided herein are written on paper or stored on a portable data storage device. The portable data storage device may be, for example, a CD, DVD, USB drive, or memory card.

In embodiments, a kit provided herein comprising instructions for releasing blood from a subject's digit according to any method provided herein may further contain one or more of a blood collection device, a piercing device, or a model hand or digit.

BRIEF DESCRIPTION OF THE DRAWINGS

In the drawings,

FIG. 1 shows a view of a hand (1A), views of a hand of a technician gripping a subject's digit according to embodiments of methods provided herein (1B, 1D, and 1E), and a view of a distal phalanx with exemplary possible piercing sites (1C).

It should be understood that the drawings and elements therein are for exemplary illustrative purposes only, and not be construed as limiting in any way.

DETAILED DESCRIPTION

Provided herein are methods for releasing blood from a subject, methods for teaching a technician to obtain blood from a subject, and kits for releasing blood from a subject.

While the invention includes various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims.

Figure 1:
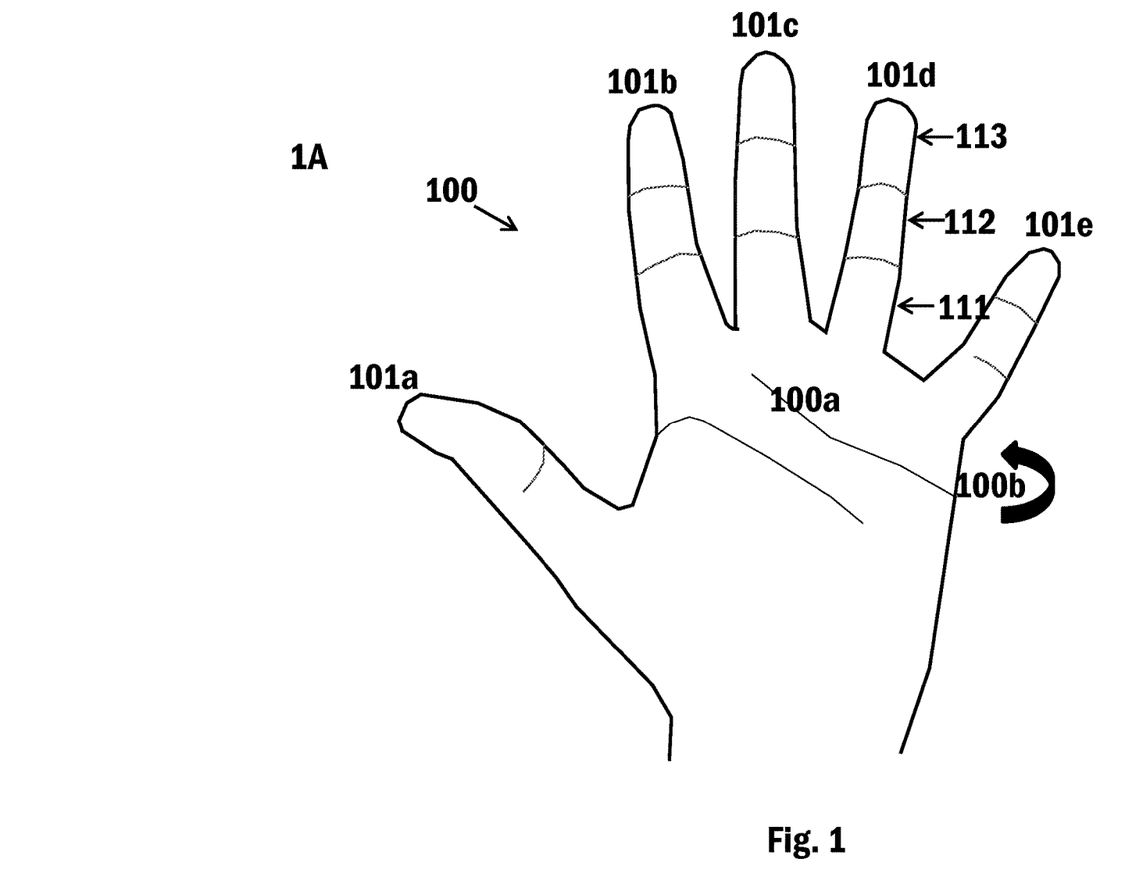

Referring now to FIG. 1, one embodiment of a method provided herein will now be described. A subject may have a hand 100 comprising a plurality of digits 101a (thumb), 101b (index finger), 101c (middle finger), 101d (ring finger), and 101e (small finger) (FIG. 1A). A digit 101 may comprise a proximal phalanx 111, an intermediate phalanx 112, and a distal phalanx 113 (FIG. 1A). A hand 100 may have at two primary sides: a palm side 100a and a fingernail side 100b.

In one non-limiting example, pressure may be applied to one or more of the proximal phalanx 111, the intermediate phalanx 112, or the distal phalanx 113 of the digit (FIG. 1B). In some embodiments, pressure is applied to all three of the proximal phalanx 111, the intermediate phalanx 112, and the distal phalanx 113 of the digit. In some embodiments, pressure is applied to the proximal phalanx 111 and the intermediate phalanx 112. In some embodiments, pressure is applied to the proximal phalanx 111 and the distal phalanx 113. In some embodiments, pressure is applied to the proximal phalanx 111 and one or both of the intermediate phalanx 112 and the distal phalanx 113. In some embodiments, pressure is applied to the intermediate phalanx 112 and the distal phalanx 113.

Pressure may be applied to two or more of the phalanges in any sequential order. In some embodiments, pressure is first applied to the proximal phalanx 111, followed by pressure being applied to one or both of the intermediate phalanx 112 and the distal phalanx 113. In some embodiments, pressure is first applied to one or both of the intermediate phalanx 112 and the distal phalanx 113, followed by pressure being applied to the proximal phalanx 111. In some embodiments, pressure is applied to two or all three of the phalanges at the same time.

Once pressure is applied to a phalanx of a digit, pressure may be maintained on the phalange. Pressure may be maintained on a phalanx for any length of time. For example, pressure may be maintained for at least 1, 2, 3, 4, 5, 6, 7, 8, 9, 10, 15, 20, or 30 seconds. In embodiments, pressure is maintained for no more than 2, 3, 4, 5, or 10 minutes. Pressure on a phalanx may be maintained at the same level of intensity as when originally applied, or it may increase or decrease. It should also be understood that pressure can be selected so that pressure on one phalanx may be greater than pressure on another phalanx. By way of non-limiting example, one embodiment may have greater pressure placed on the proximal phalanx to ensure that bodily fluid remains within the digit while pressure on the intermediate and/or distal phalanx may be at a less pressure so that that a desired flow of bodily fluid such as blood is released from the subject.

Pressure may be released from a phalanx. In some embodiments, during a method provided herein, pressure may be applied to and released from a phalanx multiple times. For example, in some embodiments, pressure may be applied to and released from a phalanx at least 2, 3, 4, 5, 6, 7, 8, 9, 10, 15, 20, 25, 30, 35, 40, 45, 50, 75, 100, 200, 300, 400 or 500 times. In embodiments, at least 1, 2, 3, 4, 5, 6, 7, 8, 9, 10, 15, 20, 30, or 60 seconds may pass between when pressure is released from a phalanx and then re-applied to the phalanx. In embodiments, no more than 2, 3, 4, 5, 6, 7, 8, 9, 10, 15, 20, 30, or 60 seconds may pass between when pressure is released from a phalanx and then re-applied to the phalanx. In embodiments, at least 1, 2, 3, 4, 5, 6, 7, 8, 9, 10, 15, 20, 30, or 45 seconds and no more than 2, 3, 4, 5, 6, 7, 8, 9, 10, 15, 20, 30, or 60 seconds may pass between when pressure is released from a phalanx and then re-applied to the phalanx, wherein it should be understood that the maximum time period is greater than the minimum time period. In some embodiments, pressure may be released from a first phalanx of a digit while pressure is maintained on a second phalanx of the same digit. In some embodiments, pressure may be maintained on a first phalanx of a digit while pressure is applied to and then released from a second phalanx of the same digit. In some embodiments, pressure may be maintained on a first phalanx of a digit while pressure is released from a second phalanx and then applied to a second phalanx of the same digit. For example, in embodiments, pressure may be maintained on a proximal phalanx 111 of a digit while pressure is applied to or released from an intermediate phalanx 112 of the same digit.

In embodiments, during one or more steps of a method provided herein, pressure may be released from all phalanxes of a pierced digit. For example, pressure may be applied to one or more phalanxes of a digit according to one or more steps provided herein, followed by releasing pressure from all phalanxes of the digit, followed by reapplying pressure to one or more phalanxes of the pierced digit. In embodiments, a digit may be pierced according to a method provided herein at the start of a method which involves one or more rounds of applying, releasing, and re-applying pressure to a digit. The cycle of applying, releasing, and re-applying pressure to a digit may be repeated any number of times. For example, in some embodiments, pressure may be applied to and released from a digit at least 2, 3, 4, 5, 6, 7, 8, 9, 10, 15, 20, 25, 30, 35, 40, 45, 50, 75, 100, 200, 300, 400 or 500 times. In embodiments, at least 1, 2, 3, 4, 5, 6, 7, 8, 9, 10, 15, 20, 30, or 60 seconds may pass between when pressure is released from a digit and then re-applied to the digit. In embodiments, no more than 2, 3, 4, 5, 6, 7, 8, 9, 10, 15, 20, 30, or 60 seconds may pass between when pressure is released from a digit and then re-applied to the digit. In embodiments, at least 1, 2, 3, 4, 5, 6, 7, 8, 9, 10, 15, 20, 30, or 45 seconds and no more than 2, 3, 4, 5, 6, 7, 8, 9, 10, 15, 20, 30, or 60 seconds may pass between when pressure is released from a digit and then re-applied to the digit. Releasing all pressure from a pierced digit at one or more intervals of a method provided herein may be advantageous, for example, in that during an interval in which pressure is not applied to the digit, blood may flow into the digit, thus increasing the volume of blood in the digit. The increased volume of the blood in the pierced digit may result in faster release of blood from the pierced digit or increased volume of blood released from the pierced digit.

In embodiments, pressure may first be applied to a proximal phalanx of a subject's digit. Upon applying pressure to the proximal phalanx, pressure may be maintained, for at least a first set amount of time, such as, for example 1, 2, 3, 4, 5, 6, 7, 8, 10, 15, 20, or 30 seconds. After the passage of the first set amount of time, pressure may be applied to one or both of an intermediate phalanx and distal phalanx of the digit. When pressure is applied to one or both of an intermediate phalanx and distal phalanx, it may be maintained, for example, for at least a second set amount of time, such as, for example, 1, 2, 3, 4, 5, 6, 7, 8, 10, 15, 20, or 30 seconds. A digit may be pierced before, during, or after application of pressure to the digit. In embodiments, blood may be collected after pressure is maintained on one or both of an intermediate phalanx and distal phalanx for a second set amount of time.

Pressure may be applied to a phalanx of a digit by various structures, including but not limited to, for instance, the fingers of a hand of a human technician, an elastic or inelastic strap, a device comprising a rigid surface, or an inflatable device. A hand of a human technician may comprise a thumb, an index finger, a middle finger, a ring finger and a small finger. In some embodiments, if pressure is applied to two or more phalanges of the same digit, the same type of structure (e.g. fingers of a hand) applies pressure to the two or more phalanges. In some embodiments, if pressure is applied to two or more phalanges of the same digit, different types of structures (e.g. fingers of a hand and an inflatable device) apply pressure to the two or more phalanges.

References herein to a "technician", a "human technician", or the like refer to any person who may perform a method provided herein to extract blood from a subject's finger. Thus, a "technician" may include, for example, a phlebotomist, a doctor, a nurse, or other health care professional. A "technician" may have one or more types of license relating to health care, or may be unlicensed. A "technician" may include a person working under the direction of a phlebotomist, doctor, or nurse.

In some embodiments, pressure may be applied to a first phalanx of a digit by the thumb 121 and index finger 122 of a hand of a human technician 120, and pressure may be applied to a second phalanx the digit by the middle finger 123 of the hand of the human technician 120 (FIG. 1B). In some embodiments, pressure may be applied to a proximal phalanx 111 of a digit by the thumb 121 and index finger 122 of a hand of a human technician 120, and pressure may be applied to one or both of the intermediate phalanx 112 and the distal phalanx 113 of the digit by the middle finger 123 of the hand of the human technician (FIG. 1B). In some embodiments, when pressure is applied to one or more phalanges of a digit by the hand of a human technician, the palm side of the hand of the human technician is in contact with the fingernail side of the hand of the subject.

In some embodiments, pressure may be applied without the application of a sliding or translational motion along the digit. In some embodiments, pressure may be applied constantly at one or more localized regions of the digit.

Figures 1, 1C:
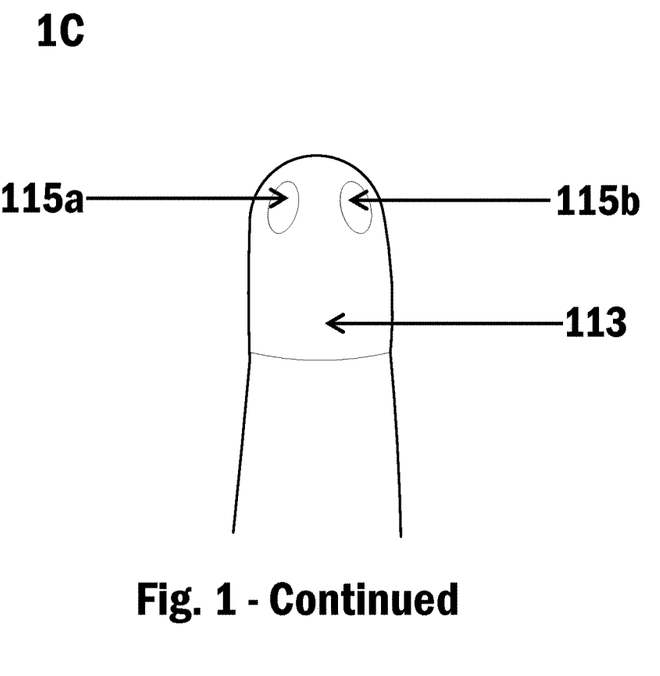

Prior to, during, or after the application of pressure to one or more phalanges of a digit, the skin of the digit may be pierced. As used herein, "pierced", "piercing", and other tenses refers to making a small opening in the skin, and may include cutting, lancing, perforating, and the like. In some embodiments, the skin of the digit may be pierced through to the dermal papillae. In some embodiments, the skin of the digit may be pierced with a piercing device. As used herein, a "piercing device" refers to a structure specialized for making a small opening in the skin or other target tissue, such as for blood testing purposes. Piercing devices that may be used with methods provided herein include, for example, a Microtainer® Contact-Activated Lancet (Beckton, Dickinson, and Company), Safe T Lance Plus (Arkray), Accu-Chek® lancing device (Roche) or SurgiLance® safety lancet (MediPurpose). Piercing devices may be automatic or manual. Piercing devices may use various structures for making an opening in the skin, such as a blade or a needle. In some embodiments, the skin of the digit may be pierced with a needle. A needle may be hollow or solid. In embodiments, a needle may have a gauge of 10, 15, 17, 19, 20, 21, 22, 23, 24, 25, 26, 27, 28, 29, 30 or higher. In embodiments, a needle may penetrate to a depth of no more than 1, 1.1, 1.2, 1.3, 1.4, 1.5, 1.6, 1.7, 1.8, 1.9, 2.0, 2.1, 2.2, 2.3, 2.4, or 2.5 millimeters. In some embodiments, the distal phalanx 113 of a digit may be pierced. In some embodiments, a site on the periphery (115a, 115b) of the distal phalanx 113 may be pierced (FIG. 1C). For example, a site on the periphery of the distal phalanx may be halfway between the center of the pad on the distal phalanx 113 and side of the finger, towards the subject's index finger (site 115a) or small finger (site 115b).

In some embodiments, pressure may be applied to and maintained on one or more phalanges of a digit prior to or during piercing the digit. Application of pressure to one or more phalanges of a digit prior to or during piercing the digit may, for example, reduce the sensation of pain associated with piercing the digit for a subject or increase the rate of blood release from the digit. In some embodiments, pressure may be applied to a proximal phalanx of a digit by the thumb 121 and index finger 122 of a hand of a human technician 120, and pressure may be applied to one or both of the intermediate phalanx 112 and the distal phalanx 113 of the digit by the middle finger 123 of the hand of the human technician prior to or during piercing the digit with a piercing device 125 (FIG. 1D). Optionally, some embodiments may apply pressure to the distal phalanx 113 for at least a preset period of time prior to any tissue penetrating event. The preset time may be, for example, at least 2, 3, 5, 8, 10, 15, 20, or 30 seconds.

In some embodiments, prior to piercing the digit, the digit or a part thereof may be warmed. A digit may be warmed, for example, by contacting the digit with an object having a temperature of at least 25, 30, 35, 40, 45, or 50° C. In some embodiments, a digit may be warmed by contacting the digit with an object having a temperature of at least 25, 30, 35, 40, 45, or 50° C. and no greater than 30, 35, 40, 45, 50, 55, 60, 65, 70, 75, 80, or 85° C. Objects which may be used to warm a digit may include, for example, electric heating pads, pads containing an exothermic chemical reaction, and warmed objects (e.g. towels, metal objects, plastic objects, and the like). It should be understood that some of these objects may be self-warming devices, or optionally, these objects are not self-warming but are instead warmed in a separate device prior to being used by the subject. In embodiments, a warming object may be wrapped around a digit, rested on a digit, or serve as a surface for receiving a digit. In embodiments, before, during, or after the piercing of a digit, a subject may grasp or support a warming object in the hand supporting the digit which is pierced. In embodiments, contacting the subject's hand with a warming object before and/or during extraction of blood from the pierced digit may increase the flow of blood to the digit and may, for example, decrease the collection time for obtaining a selected volume of blood, or increase the volume of blood released from the digit.

In some embodiments, a relatively large quantity of blood may be released from a subject's digit with a method provided herein. In some embodiments, at least 10, 20, 30, 40, 50, 60, 70, 80, 90, 100, 110, 120, 130, 140, 150, 160, 170, 180, 190, 200, 210, 220, 230, 240, 250, 300, 350, 400, 450, or 500 microliters of blood may be released from a subject's digit with a method provided herein. With a method provided herein, at least 10, 20, 30, 40, 50, 60, 70, 80, 90, 100, 110, 120, 130, 140, 150, 160, 170, 180, 190, 200, 210, 220, 230, 240, 250, 300, 350, 400, 450, or 500 microliters of blood may be released from a subject's digit after the digit is pierced with a needle having a gauge of 21, 22, 23, 24, 25, 26, 27, 28, 29, 30, or higher.

In addition, with methods provided herein, a relatively large quantity of blood may be released from a subject's digit rapidly. In some embodiments, at least 10, 20, 30, 40, 50, 60, 70, 80, 90, 100, 110, 120, 130, 140, 150, 160, 170, 180, 190, 200, 210, 220, 230, 240, 250, 300, 350, 400, 450, or 500 microliters of blood may be released from a subject's digit within 15, 30, or 45 seconds or 1, 2, 3, 4, 5, 10, 15, 20, 25, 30, 35, 40, 45, 50, 55, 60, 70, 80, 90, 100, 110, 120, 180, or 240 minutes of piercing the subject's digit.

In some embodiments, blood released from a digit according to a method provided herein may be contacted by a channel of a blood collection device 127 (FIG. 1E). When blood released from a digit is contacted by a channel of a blood collection device 127, pressure may continue to be applied by one or more fingers of a human technician to the digit. In some embodiments, when blood released from a digit is contacted by a channel of a blood collection device 127, pressure may be applied to a proximal phalanx of a digit by the thumb 121 and index finger 122 of a hand of a human technician 120, and pressure may be applied to one or both of the intermediate phalanx 112 and the distal phalanx 113 of the digit by the middle finger 123 of the hand of the human technician. In some embodiments, the channels of a blood collection device will be maintained at a horizontal orientation when in contact with blood released from a digit. In some embodiments, blood released from a digit may be contacted with a channel of a blood collection device as described in U.S. Provisional Patent Application No. 61/697,797 filed Sep. 6, 2012 or U.S. Provisional Patent Application No. 61/786,351 filed Mar. 15, 2013, both of which are herein incorporated by reference in their entireties for all purposes. In some embodiments, the blood collection device is held at an orientation such as but not limited to horizontal, to minimize introduction of air bubbles into the device.

In some embodiments, a technician having a first hand and a second hand will use the first hand to grip the digit of a subject in one or more of the manners described herein, and the second hand to hold a blood collection device, and contact the released blood from the digit with the blood collection device. Optionally, a technician having a first hand and a second hand will use the first hand and second hand to grip the digit of a subject, such as one hand contacting a proximal phalanx while the second hand hold a different phalanx on the same digit, while a holder or other apparatus holds a blood collection device, and the technician contact the released blood from the digit with the blood collection device.

Figure 2:
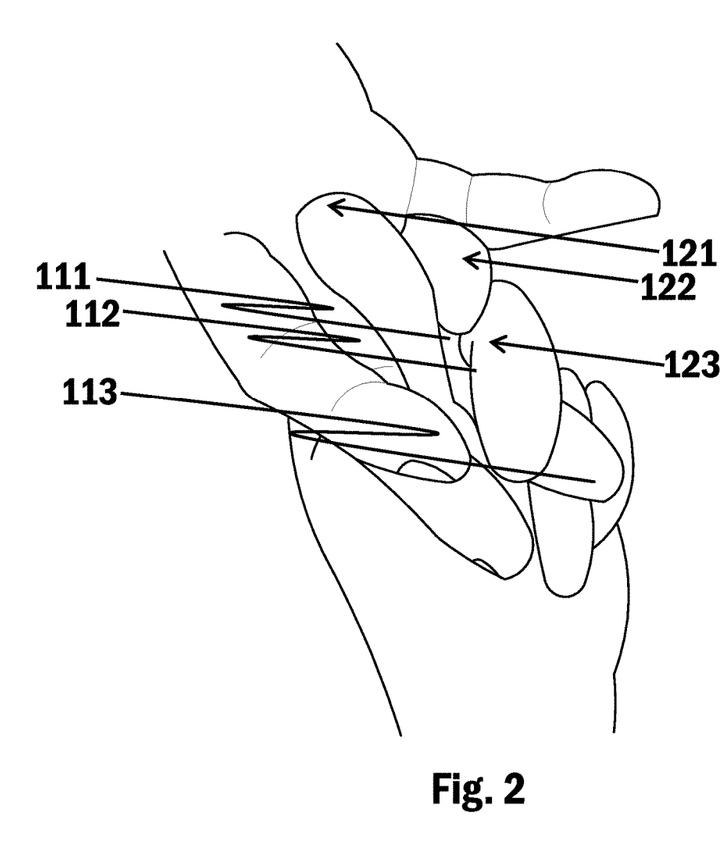
FIG. 2 shows a view of a hand of a technician gripping a subject's digit according to an embodiment of a method provided herein.

Methods described herein may be performed by both right and left-handed technicians. FIG. 2 provides a view of a hand of a left-handed technician gripping a subject's digit according to an embodiment of a method provided herein. A left-handed human technician may apply pressure with a left-hand thumb 121 and index finger 122 to a proximal phalanx 111 of a subject's digit, and may apply pressure with a left-hand middle finger 123 to one or both of the intermediate phalanx 112 and the distal phalanx 113 of the subject's digit.

Figure 3:
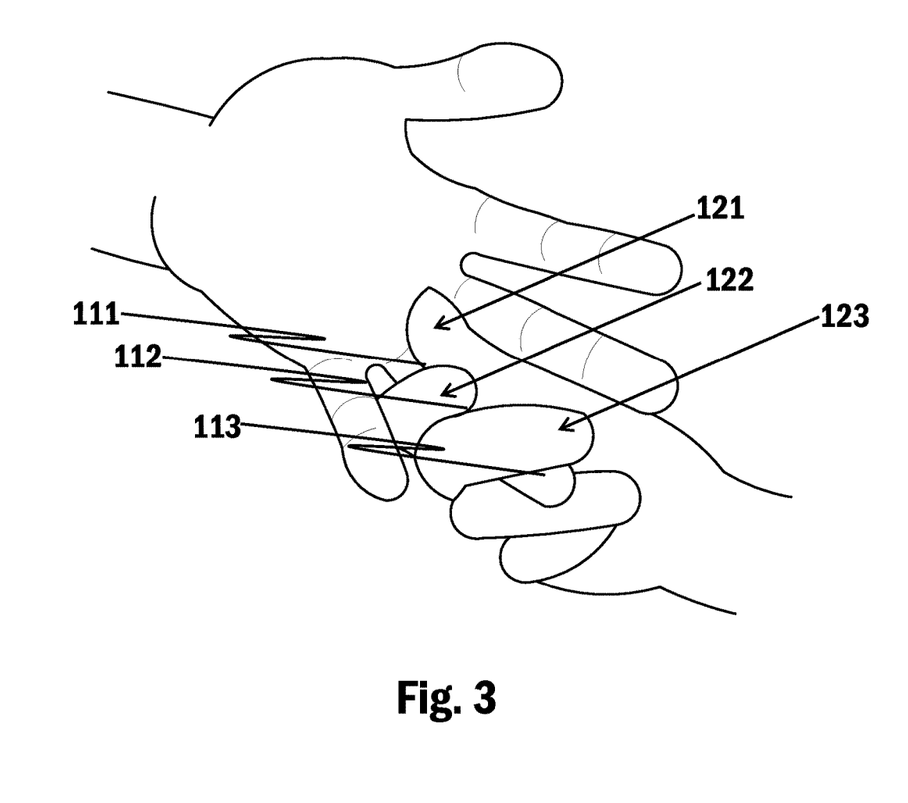
FIG. 3 shows a view of a hand of a technician gripping a subject's digit according to an embodiment of a method provided herein.

Methods described herein may be performed on any digit of a subject's hand or foot. In some embodiment, methods described herein may be performed in a subject's thumb, index finger, middle finger, ring finger, or small finger. FIG. 3 provides a view of a hand of a technician gripping a subject's ring finger according to an embodiment of a method provided herein. A human technician may apply pressure with a thumb 121 and index finger 122 to a proximal phalanx 111 of a subject's ring finger, and may apply pressure with a middle finger 123 to one or both of the intermediate phalanx 112 and the distal phalanx 113 of the subject's ring finger.

Figure 4:
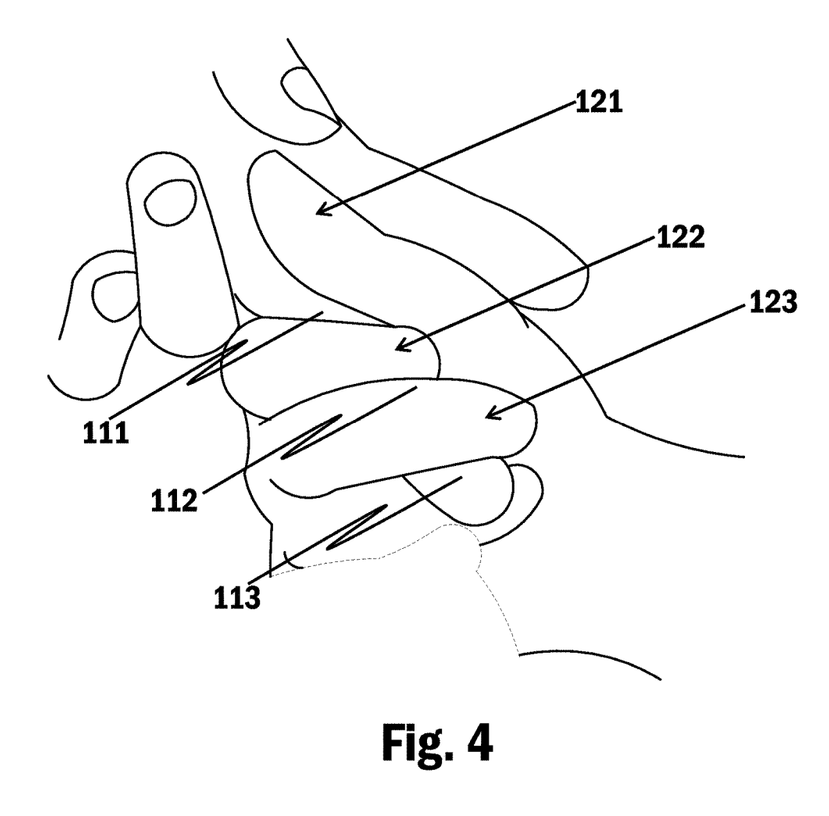
FIG. 4 shows a view of a hand of a technician gripping a subject's digit according to an embodiment of a method provided herein.

FIG. 4 provides a view of a hand of a technician gripping a subject's digit according to another embodiment of a method provided herein. A human technician may apply pressure with a thumb 121 to a proximal phalanx 111 of a subject's digit, may apply pressure with an index finger 122 to an intermediate phalanx 112 of the subject's digit, and may apply pressure with a middle finger 123 to the distal phalanx 113 of the subject's finger. In some embodiments, pressure can be applied to the proximal phalanx by a substantial, but not complete, application of pressure around a perimeter of the proximal phalanx. By way of non-limiting example, pressure is applied to at least about 70% of the perimeter of the phalanx. Optionally, pressure is applied to at least about 30%, 40%, 50%, 60%, 70%, 80%, 90%, or 100% of the perimeter of the phalanx.

In embodiments, methods provided herein may involve a technician establishing a tourniquet-like structure on a proximal phalanx of a subject's digit, and the technician intermittently applying pressure to one or both of an intermediate phalanx or distal phalanx of the subject's digit. The subject's digit may be pierced before, during, or after applying pressure to the subject's digit. In embodiments, the tourniquet-like structure may be established by the technician's thumb and index finger. In embodiments, the technician intermittently may use his or her middle finger to apply pressure to one or both of the subject's intermediate phalanx or distal phalanx. In embodiments, a technician may first establish a tourniquet-like structure on a proximal phalanx of a subject's digit, followed by the technician intermittently applying pressure to one or both of an intermediate phalanx or distal phalanx of the subject's digit.

In embodiments, methods provided herein may be performed wherein the subject's hand is positioned such that the thumb of the subject's hand is at a higher elevation than one or more other digits of the subject's hand. The subject's hand may be positioned with its thumb at a higher elevation than one or more other digits of the hand for some or all steps of a method provided herein. In embodiments, the subject's hand may be positioned with its thumb at a higher elevation than one or more other digits of the hand during the majority of the time of the performance of a method provided herein (e.g. greater than 50, 60, 70, 80, or 90% of the time). Similarly, the subject's hand may be positioned during some or all steps of a method provided herein such that the distal phalanx 113 of the subject's thumb is at a higher elevation than the proximal phalanx 111 or intermediate phalanx 112 of the subject's thumb. In embodiments, the subject's hand may be positioned with its thumb at a higher elevation than one or more other digits of the subject's hand or with the distal phalanx 113 of its thumb at a higher elevation than the proximal phalanx 111 or intermediate phalanx 112 of the subject's thumb when blood is obtained from a digit other than the subject's thumb according to a method provided herein. For example, the subject's thumb may be positioned at a higher elevation than one or more of the other digits of the subject's hand when blood is obtained from the subject's middle finger or ring finger according to a method provided herein. Having the subject's thumb and optionally, one or more other digits at an elevation above a pierced digit from which blood is extracted may, for example, increase the flow of blood to pierced digit and thus may decrease collection time or increase the volume of blood released from the pierced digit.

A subject's hand is supported by a subject's arm. An arm may include an upper arm and a forearm, in which the upper arm and the forearm are connected by the elbow, the upper arm is the region between the shoulder and elbow, and the forearm is the region between the elbow and the hand. In embodiments, during the performance a method provided herein, the arm which supports the hand containing the digit from which blood is extracted may be positioned such that the upper arm and forearm define an angle, with the vertex of the angle being at the elbow. In embodiments, during some or all steps of a method provided herein, the arm may be bent such that the upper arm and forearm define an angle of 90 degrees or more. In embodiments, the arm may be positioned such that arm is essentially straight, in which the upper arm and forearm define an angle between 170 and 190 degrees (e.g. 180 degrees). In embodiments, the arm may be positioned such that the upper arm and forearm define an angle between 90 and 180 degrees. In embodiments, the arm may be positioned such that the upper arm and forearm define an angle of at least 30, 35, 40, 45, 50, 55, 60, 65, 70, 75, 80, 85, 90, 95, 100, 105, 110, 115, 120, 125, 130, 135, 140, 145, 150, 155, 160, 165, 170, or 175 degrees and no more than 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, or 190 degrees. Certain angles of an arm supporting a hand having a pierced digit may increase the flow of blood to the pierced digit and thus may decrease collection time or increase the volume of blood released from the pierced digit. For example, in embodiments, positioning an arm supporting a hand having a pierced digit such that the upper arm and forearm define an angle of at least 90 degrees may increase the flow of blood to the pierced digit, as compared to positioning the arm such that the upper arm and forearm define an angle of less than 90 degrees.

In embodiments, during a method provided herein involving a subject and a technician, the subject may be positioned such that if the subject's upper arm and forearm define an angle between 90 and 180 degrees, the technician will be able to easily access a digit of the subject's hand. This set-up may optionally be achieved, for example, if the subject is seated in a seat having a seat base which is at a higher elevation than the seat base of a seat in which the technician sits, or if the subject is seated in a seat having a reclining back support. Commonly, if a subject who is seated in an upright position and at an equal elevation to a technician extends his or her arm such that the upper arm and forearm define an angle between 90 and 180 degrees, the subject's hand supported by the arm may be positioned relatively far from the subject's torso (e.g. near the ground), and may be relatively difficult for a technician to access. However, if, for example, the subject is seated at an elevation slightly above the technician, or is permitted to recline, the technician may be able to easily access the subject's hand when the subject's arm is extended such that the upper arm and forearm define an angle between 90 and 180 degrees.

In embodiments, during a method provided herein involving a technician, the technician may be situated such that all devices needed by the technician for the performance of the method are within easy reach of the technician, such that the technician does not need to stand up or lean far during the performance of the method. In embodiments, the technician may be situated in an ergonomically-friendly environment, such that the technician may be able to assist in the extraction of blood from multiple subjects without developing a repetitive-motion related injury. For example, a biohazard waste container may be situated near the technician so that the technician can dispose of biohazard waste without needing to perform a substantial bodily movement. In one non-limiting example, the height of the chair that the technician is sitting in is adjusted such that the subject's target tissue in the phalanx or the like is at a level that pre-disposes the subject to position their arm or target body part in a configuration as previously described herein to improve sample collection. This can be achieved in part by having the technician sitting at a level where he or she will manipulate the subject's target tissue to guide, gently, pull, or gently bend it in the desired manner to improve sample collection as discussed herein. Optionally, instead of adjusting the technician's sitting height, other embodiments can have a chair height and/or a reduced height hand rest that encourages the desired body part configuration. In one non-limiting example, the reduced height hand rest is at or below the seat cushion level of the chair. Some embodiments may have the subject leaning towards the side of the chair with the hand rest, wherein the leaning may encourage a low, straight arm configuration.

Optionally, some embodiments may use one or more devices that is a mechanical or other apparatus (e.g. a tourniquet) applied to the subject at one or more, two or more, or other number of locations to create the desired pressure and location profile. Optionally, the surface(s) used to apply pressure to the digit are sterile and waterproof surface(s). It should be understood that in some embodiments, a collection device contacts only the bead of blood or bodily fluid on the surface of the digit, without directly contacting the surface of the digit. Optionally, some embodiments may use a surface that applied pressure over portions of two or more phalanges and is not confined to only applying pressure to a single phalanx. Optionally, some embodiments may apply pressure on both a palm-side and a fingernail-side of the digit at each of the phalanges. By way of non-limiting example, one may place pressure on the palm-side and the fingernail-side of the proximal phalanx while pressure at one of the other phalanx may be only on one side of the digit. Optionally, one may place pressure on the palm-side and the fingernail-side of the proximal phalanx while pressure at one of the other phalanges is also on the palm-side and the fingernail-side of the phalanx. Optionally, one may place pressure on the palm-side and the fingernail-side of the proximal phalanx while pressure at one of the other phalanges is in a longitudinally offset manner where the location of pressure on the fingernail-side of the phalanx does not fully overlap with location of pressure on the palm-side of the phalanx.

In embodiments, a subject may be provided with a drink before initiating a method provided herein. The drink may be water, juice, milk, or other beverage. A volume of at least 5 ml, 10 ml, 25 ml, 50 ml, 100 ml, 200 ml, or 300 ml may be provided to a subject. The drink may be provided at least 1, 2, 3, 4, 5, 6, 7, 8, 9, 10, 15, 20, 30, 45, or 60 minutes before initiating a method provided herein. In some circumstances, a subject may release more blood or release blood faster during a method provided herein when the subject has consumed a drink before the initiation of the method. It should be understood that the beverage may be given to the subject at at least a minimum amount of time prior to the bodily fluid sample collection event. By way of non-limiting example, a workflow may be implemented wherein the beverage or liquid is provided to the user as part of an appointment check-in process such that there is at least a waiting period, of an amount previous recited above, after check-in before sample collection occurs or before the subject is taken from a waiting location into the sample collection location. Optionally, one workflow may be implemented wherein the liquid or beverage is given after the user has been verified for the appointment and after payment, whether by insurance and/or directly by the subject, has been collected. As previously recited, the volume of the drink may be a minimum volume that is the same for all patients or patient classes. Optionally, the volume of the drink container, the volume of fluid dispensed into the container, and/or a level line or other marker indicating the amount of fluid the subject should consume, can be selected based on one or more factors about the subject, including but not limited to age, weight, height, time of day, medical background, type of test to be conducted, medications being taken, or the like. In an example, an amount that the subject should consume, can be printed onto a label that is then attached to the beverage container to show the minimum amount to be consumed. It should also be understood that the beverage, although typically water in most embodiments, can also be a beverage with controlled amounts of sugar or other ingredient based on the condition(s) known about the subject. In some examples, a patient may be given a selection of beverages to choose from. In embodiments, upon check-in or registering for a blood collection, a patient may be given a token, code, key, or other pass which the patient may then present at a beverage-dispensing device or location (e.g. a vending machine or a personnel-staffed beverage counter) in order to receive a beverage.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. It should also be understood that while the invention provided herein has been described herein using a limited number of terms and phrases for purposes of expediency, the invention could also be described using other terms and phrases not provided herein which also accurately describe the invention. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. As used in the description herein and through the claims that follow, a first object described as containing "at least a portion" of a second object may contain the full amount of/the complete second object. As used in the description herein and throughout the claims that follow, the terms "comprise", "include", and "contain" and related tenses are inclusive and open-ended, and do not exclude additional, unrecited elements or method steps. Also, the presence of broadening words and phrases such as "one or more," "at least," "but not limited to" or other like phrases in some instances shall not be read to mean that the narrower case is intended or required in instances where such broadening phrases may be absent. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2013-14 Theranos, Inc.

We claim:

1. A method by a technician for releasing blood from a subject, comprising:
   gripping only one digit of the subject using a multi-pressure zone technique, wherein gripping applies grip pressure simultaneously to i) a proximal phalanx of the digit between two digits of a hand of the technician at first zone and ii) one or both of an intermediate phalanx and a distal phalanx of the digit between another two digits of said hand of the technician at a second zone, and,
   while pressure is maintained on the proximal phalanx and said one or both of the intermediate phalanx and the distal phalanx, piercing a site on the distal phalanx, wherein blood is released from the site pierced on the distal phalanx;
   contacting released blood with a blood collection device;
   after the distal phalanx has been pierced, releasing all of said pressure from the proximal phalanx and said one or both of the intermediate phalanx and distal phalanx,
   reapplying and maintaining pressure to the proximal phalanx, and
   while pressure is maintained on the proximal phalanx, reapplying and maintaining pressure to one or both of the intermediate phalanx and the distal phalanx, wherein blood is released from the site pierced on the distal phalanx and is contacted again by the blood collection device.

2. The method of claim 1, wherein pressure on the proximal phalanx is maintained without using a sliding or translational motion to apply pressure against the digit.

3. The method of claim 1, wherein pressure on said one or both of the intermediate phalanx and the distal phalanx is maintained without using a sliding or translational motion to apply pressure against the digit.

4. The method of claim 1, wherein pressure is applied to the digit of the subject in a sequential manner, wherein pressure is first applied to the proximal phalanx and then pressure is applied to said one or both of the intermediate phalanx and the distal phalanx.

5. The method of claim 1, wherein at least one of i) the applying and maintaining of pressure to the proximal phalanx or ii) the applying and maintaining of pressure to said one or both of the intermediate phalanx and distal phalanx, is performed by one or more fingers of a hand of a human technician.

6. The method of claim 5, wherein both i) the applying and maintaining of pressure to the proximal phalanx and ii) the applying and maintaining of pressure to said one or both intermediate phalanx and distal phalanx, is performed by one or more fingers of a hand of a human technician.

7. The method of claim 5, wherein the fingers are selected from a thumb, an index finger, a middle finger, a ring finger, and a small finger, and wherein the applying and maintaining pressure to the proximal phalanx is performed by fingers comprising the thumb and index finger.

8. The method of claim 5, wherein the applying and maintaining pressure to said one or both intermediate phalanx and distal phalanx is performed by one or more fingers comprising the middle finger.

9. The method of claim 1, further comprising warming the digit before the applying pressure to or piercing the digit.

10. The method of claim 1, wherein during the method a total of at least 50 microliters blood is released from the digit of the subject.

11. The method of claim 10, wherein during the method a total of at least 100 microliters blood is released from the digit of the subject.

12. The method of claim 1, wherein during the majority of the duration of the method, the distal phalanx is maintained at a lower elevation than the elevation of the proximal phalanx.

13. The method of claim 1, wherein the digit is pierced with a needle having an outer diameter of 1.1 mm or smaller.

14. The method of claim 1, further comprising contacting the released blood with a channel of the blood collection device.

15. The method of claim 14, wherein the channel of the blood collection device has a perimeter of no greater than 15 millimeters.

16. A method of teaching a technician to obtain blood from a subject's digit, the method comprising providing the technician with instructions for releasing blood from a subject's digit according to the method of claim 1.

17. A kit for releasing blood from a subject, the kit comprising instructions for releasing blood from a subject's digit according to the method of claim 1, wherein the instructions are written on paper or stored on a portable data storage device and at least one blood collection device.

18. The kit of claim 17, wherein the kit further comprises a piercing device.

* * * * *